United States Patent [19]

Herrmann

[11] 4,020,159
[45] Apr. 26, 1977

[54] METHODS OF AND MEDICATIONS FOR TREATING CARDIAC DISORDERS BY USING STROPHANTHIN

[75] Inventor: Joseph Peter Herrmann, Wiesbaden, Germany

[73] Assignee: Apotheker A. Herbert K.G., Fabrik Pharmazeutischer Praparate Wiesbaden, Wiesbaden, Germany

[22] Filed: Oct. 8, 1974

[21] Appl. No.: 513,151

[52] U.S. Cl. .............................................. 424/180
[51] Int. Cl.$^2$ ..................................... A61K 31/70
[58] Field of Search ................................... 424/180

[56] References Cited

UNITED STATES PATENTS 2,981,657   4/1961   Hall ................................... 424/180

OTHER PUBLICATIONS

Manfred Von Ardenne et al., Forschungsinstitut Manfred Von Ardenne, DDR–8051, Dresden Weisser Hirsch, Zeppelinstasse 7, 1971.

*Primary Examiner*—Albert T. Meyers
*Assistant Examiner*—Daren M. Stephens
*Attorney, Agent, or Firm*—Strauch, Nolan, Neale, Nies & Kurz

[57] ABSTRACT

Methods of treating cardiac disorders by the oral administration of a g- or k-strophanthin, and medications for use in such methods.

10 Claims, No Drawings

METHODS OF AND MEDICATIONS FOR TREATING CARDIAC DISORDERS BY USING STROPHANTHIN

This invention relates to the treatment of cardiac disorders and, more specifically, to the treatment of such disorders with a g- or k-strophanthin dispersed in an oleophilic vehicle or carrier.

G- and k-strophanthins are glycosides obtained from the seeds of *Strophanthus gratus* and *Strophanthus kombé*, respectively. Stropanthins have on occasion in the past been used intravenously and orally as myocardial tonics and stimulants in a manner akin to digitalis. As heretofore administered, they are not tolerated well by many patients. Notable side effects are diarrhea and, when administered orally, irritation of the mucous membranes.

Other important disadvantages of the heretofore employed strophanthin medications are a lack of effectiveness in some cases and a wide variation in degree of effectiveness (over 10:1 according to one investigator).

To be effective and to produce consistent results when administered orally, strophanthins must be used in formulations containing a relatively high concentration of the glycoside. This is because the primary effect of a strophanthin is obtained only if a relatively high threshhold concentration of the glycoside is attained in the myocardium in a short time; and, to produce such a concentration, it is necessary that a medication with a high concentration of the strophanthin be administered.

Previously, this was not recognized; and the oral medications containing these glycosides heretofore used were often ineffective or produced erratic results because the concentration of the active principle was too low.

Furthermore, when administered orally, the effectiveness of strophanthins depend to at least a considerable degree upon the rapidity with which they can be resorbed through the mucous membrane. This is why the heretofore used strophanthin tablets and pills have not proven particularly effective, especially in emergency situations where fast response is essential. When compressed into a tablet or pill the glycoside is liberated too slowly for an optimum effect to be obtained.

I have now invented certain novel, orally administrable, strophanthin medications which do not have the disadvantages just discussed. In my novel galenic formulations the strophanthin in the form of a finely divided powder is uniformly dispersed in a liquid, oleophilic carrier or vehicle.

One advantage of this novel type of formulation is that high concentrations of the strophanthin can be obtained. Another is that, because the strophanthin is present in a finely divided and dispersed state, resorption proceeds rapidly when the medication is administered. Effectiveness and consistency of results are obtained.

Furthermore, my novel preparations are tolerated better by the patient than has typically heretofore been the case. They have a markedly lower irritating effect on mucous tissue and are less apt to cause diarrhea.

Also, strophanthins administered in accord with the principles of the present invention remain effective for substantially longer periods of time than do those administered intravenously, and the danger of an overdose being administered is virtually eliminated.

There are several criteria which the oleophilic vehicle of my novel medications must or desirably should possess. It must be capable of keeping uniformly distributed a high concentration of the medicinally active principle and of rapidly liberating it when the medication is taken. This results in a time-optimized resorption which produces a concentration of the strophanthin capable of exerting the wanted triggering action in the myocardial capillaries.

Also, the vehicle should be capable of mitigating irritation of mucous tissue, and it must be chemically inert relative to the active principle.

I have found that these criteria can be met by employing vehicles which contain from 60–90 percent by weight of one or more fatty oils and from 2–20 percent of a wax or mixture of waxes.

The fatty oil or oils can be considered the actual carrier material. The particular ones which are employed are not critical although those selected must be physiologically harmless, easily manageable, and physically and chemically stable. Of particular importance is that their consistency remain constant over a temperature range of approximately 25°–40° C.

I have identified hereinafter a number of vegetable oils which are satisfactory for my purposes. Animal and other fats and oils can also be used as long as they have the necessary characteristics.

The wax component of the vehicle serves to adjust and stabilize the physical properties of the vehicle, especially its consistency over the 25°–40° C. temperature range. The amount of wax used in each particular case is a function of the physical properties and the quantity of the fatty oils employed. When the fatty oils are relatively fluid in the desired temperature range, a correspondingly increased amount of wax is required to obtain the requisite viscosity.

There are several ingredients which, while not essential, can also often be employed to advantage in the oleophilic vehicles of my novel strophanthin medications. Among these are physiologically harmless emulsifiers capable of insuring that the glycoside stays uniformly dispersed and materials capable of reducing irritation of the mucous membrane during the transfer of the glycoside into the tissue. Use of the latter is particularly advantageous when an emulsifier is employed.

I have found that the emulsifier and irritation mitigating effects can both be obtained by adding a lecithin to the vehicle in an amount ranging from 2 to 20 percent based on the total weight of the vehicle. Percentages of not more than 10 percent are, however, preferred because the lecithin may begin to exert its own irritating effect on the mucous membrane as the proportion is increased above this level.

The optimum quantity of lecithin is a function of the particular type employed. For example, soy lecithin is preferably employed in an amount ranging between 3 and 7 percent.

Lecithins are particularly useful additives because the molecules have hydrophilic groups on one end and oleophilic groups on the other. As a consequence, the molecules can link to the glycoside particles through their hydrophilic groups, forming an enevlope around the glycoside particles. The envelope has the oleophilic groups of the lecithin molecule on the outside, and this promotes stability between the glycoside particles and the oleophilic, lipoid phase vehicle.

In a typical application a medication in accord with the present invention will be supplied in capsule form. When the capsule is bitten by the patient, the vehicle with the glycoside dispersed in it pours out over the mucous membrane; and the glycoside particles enveloped with lecithin molecules come into contact with the saliva-moistened and thus hydrophilic mucous membranes. This encounter of the hydrophilically moistened mucous membrane and the oleophilic envelope of the glycoside ruptures the mantle of lecithin molecules so that the glycoside is transferred into the tissue of the mucous membrane with the oleophilic vehicle shielding the glycoside from the saliva in the patient's mouth. As a result, the transfer of the glycoside from the vehicle into the tissue of the mucous membrane takes place rapidly, with a high degree of effectiveness, and with minimum irritation of the tissue.

Physiologically harmless, aromatic flavoring agents can also optionally be incorporated into the vehicle to make the medication more palatable to the patient. Examples of suitable materials are: peppermint aroma, fruit aroma, and the like. I use very small quantities of the aromatic substances — preferably just enough to hide the taste of the fatty oils and the wax and, perhaps, the lecithin.

Finally, a preservative for the fatty oils and possibly the lecithin is generally provided as an optional component to prolong the stability of the vehicle. Suitable preservatives will be obvious to those to whom this is addressed inasmuch as those physiologically harmless compounds used as food preservatives can in general be employed.

The minimum useful concentration of the glycoside in my novel medications is 3 percent based on the total weight of the formulation. Concentrations in the range of 3–6 percent and dosages of ca. 3 mg are preferred; but concentrations of up to 20 percent by weight can be employed, if desired. In all cases the concentration which will be selected will preferably be that which, for the particular vehicle and active principle, will optimize the resorption of the glycoside and yet hold irritation of the mucous membrane within limits which can be readily tolerated by the patient.

One medication in accord with the present invention (Strodival) contains 3.0 mg of pure, crystallized, finely divided, pharmacologically active g-strophanthin which satisfies the requirements of DAB 7 (German Pharmocopeia, 7th Edition).

The glycoside can be obtained (Wallich and Hook) by hot extracting de-oiled seeds of *Strophanthus gratus* with 70 percent ethanol. The alcohol is distilled from the filtered extract. The residue is dissolved in water and the solution mixed with a small quantity of lead acetate and digested with lead oxide. Lead is removed from the filtered solution with hydrogen sulfide and the liquid concentration in vacuo to a thin syrup.

The crystalline strophanthin precipitates as a finely divided powder. It is drawn off by suction and recrystallized from hot water with the addition of animal charcoal. The material is recrystallized as many times as is necessary to satisfy the requirements of DAB 7.

In Strodival, the g-strophanthin is uniformly dispersed in an oleophilic vehicle which contains, based on the total weight of the formulation:

beeswax — 3.7 percent;
partially hydrogenated vegetable oils — 39.8 percent;
hydrogenated soybean oil — 3.7 percent;
soy lecithin — 5.0 percent;
rape oil — 44.0 percent.

The Strodival balance of the formulation consists of the g-strophanthin and aromatic compounds employed to improve the taste of the composition.

The beeswax (cera flava) and rape oil I use in formulating Strodival satisfy the requiirements for purity of DAB 7 and DAB 6, respectively.

The vegetable oils in Strodival (peanut, cottonseed, soy, corn, palm) are, primarily, glycerides of the following acids:

saturated fatty acids — 18 to 21 percent;
oleic acid — 72 to 76 percent;
linoleic acid — 1.3 to 3.0 percent;
linolenic acid — 0.04 to 3 percent;
arachidonic acid — a trace at most.

The vegetable oils component of Strodival has the following characteristics:

acid number — less than 0.5;
saponification number — about 185 to 195;
iodine number — about 65 to 75;
peroxy number — less than 1.0;
melting point — about 43° to 46° C.

The partially hydrogenated vegetable oils are approved as food fats by the United States Food and Drug Administration under the designation PRIMES.

The hydrogenated soybean oil is primarily a glyceride mixture characterized by its almost exclusive content of the following saturated fatty acids:

palmitic acid — about 6 to 13 percent;
stearic acid — about 85 to 94 percent;
arachic acid — about 0.5 percent;
behenic acid — about 0.5 percent.

The characteristics of the soy lecithin are as follows:

iodine number — at least 85;
acid number — $\leqq 32$;
peroxy number — maximum 10;
density — at least 1.03 to 1.04;
phosphor content — at least 2.1 percent.

The aromatic substances employed in Strodival to make the medication more palatable are: o-benzoic acid sulfimide, peppermint oil DAB, ethyl vanillin NF, and p-methoxyacetophenone.

The Strodival vehicle is a single, clear, transparent, lipoid phase in which all components are intimately mixed. The very finely divided glycoside is dispersed in this lipoid phase by homogenizing it with the vehicle in automatic stirring apparatus of conventional character.

The g-strophanthin dispersion is encapsulated in shells prepared from a gelatin web. The shells are filled with 100 mg of the homogenized mixture (3.0 mg glycoside). Immediately thereafter, the water is removed from the shells in a drying tunnel with infrared radiation (Scherer process).

The dried shell has an approximate weight of 80 mg and consists of 67 percent gelatin USP and 33 percent glycerin DAB. It also contains 1 percent titanium dioxide (Schultz No. 1418, Color Index 77891) and 0.022 percent Cochineal Red A (Schultz No. 213, Color Index 16255) as well as 0.3 percent p-hydroxybenzoicacid-ethylester-sodium and 0.15 percent p-hydroxybenzoicacid-propylester-sodium perservatives.

The Strodival medication is taken orally. The capsules may be bitten through and masticated before swallowing to promote resorption through the mucous membrane and provide an almost immediate response. If the capsule or part of its contents are swallowed, the active principle will also or instead be resorbed through enteral tissue with less rapid results. At least one investigator considers this two-phase activity highly desirable.

Administration is not by rigid schedule but as needed to alleviate symptoms. For a permanent treatment, one or two capsules taken two to four times daily will normally suffice with higher doses being employed initially and the dosage later reduced.

For immediate treatment to suppress angina pectoris or heart collapse, two to three capsules are bitten through, chewed thoroughly, and swallowed. If necessary, the treatment can be repeated in twenty minutes, either at the same or at a reduced dosage.

The following case histories demonstrate the increased effectiveness of and increased patient tolerance to my novel strophanthin preparations. The product employed was in each case that described above (Strodival).

I INTERNIST PRACTICE IN WUERTTEMBURG, GERMANY

Case 1: P. H., 58 years old

The patient returned from 2 years of Russian captivity with dystrophy and nephritis. He had hypertonicity of the cardiogenic type for several years. An examination showed high blood pressure (200/100) and severe left insufficiency with cardiogenic hypertonicity.

Treatment with Strodival was begun in September (one capsule about three times daily). This was followed by an immediate drop in blood pressure to around 140/150 over 90. The patient became completely free of symptoms. The improvement was maintained until July of the next year. There was also a recovery from liver damage caused by years of treatment with Marcumar.

Case 2: Sch. V., 47 years old

The patient had had Weil's disease, hepatitis (twice), scarlet fever and articular rheumatism (1943). Hypertonicity has existed since then. There was an enormous left dilation with hypertrophy damage also shown in the ECG (V 5, V 6); clear accentuation of PT 2; continuous subjective heart complaints; typical cardial insomnia; and a blood pressure of 150/100 cardiogenically increased.

The first examination after Strodival medication showed a very marked improvement in the patient's general state of health, and the patient was more productive.

Case 3: W. G., 21 years old

The patient had frequent anginas, a blood pressure of 120/70, sinus arrhythmia, clear tachycardia with low voltage and numerous ECG indications of damage, and left hypertrophy.

Contrary to instructions, the patient took only one Strodival capsule per day, and feverish angina recurred. After treatment with penicillin and other medications, there was further degradation of the ECG diagnosis.

The focal diagnosis was chronic tonsillitis. A tonsillectomy was performed. The only post-treatment prescribed was Strodival. Again, only one capsule was taken daily contrary to instructions.

Nevertheless, a short time later the chamber potential had recovered to 17.5 percent; and the patient was almost completely free of complaints.

II GENERAL PRACTICE IN SWITZERLAND

Case 1: Mrs. H. J., 49 years old

Symptoms were anamnesis and cramps over the area of the heart with exertion and changes in the weather; the patient could not lie on her left side and often sweated at night and had an increased requirement for fresh air. An ECG was taken without result. The patient's blood pressure was 145/85, but there were no abnormal (objective) findings concerning the heart.

After a short-term application of Strodival (2 to 3 capsules daily), there was an almost complete disappearance of the previous complaints.

Case 2: F. B., male, 52 years old

The patient was known since 1956. He had a normal blood pressure of 110/80 at that time. Over the years, a hypertonia developed. This was successfully treated with a commercially available oral strophanthin preparation, but the patient had a poor tolerance to the medication.

Some years later the patient developed a dry cough and dyscardic cramp symptoms over the heart with radiations. The patient slept poorly and had vertigo and a blood pressure of 150/90.

One capsule of Strodival three times daily was prescribed in the place of the previously administered oral strophanthin preparation. There was no convincing improvement after 1 week. The same medication was continued. After one month the patient reported complete freedom from complaints, and his blood pressure was 140/90. He could easily take the Strodival medication three times daily.

Case 3: Mrs. K. B., born 1903

Perpetual arrhythmia with dyscardic symptoms had existed for many years. Complaints were kept within tolerable limits for a long time with Lanata and oral strophanthin.

The patient was hospitalized with a tonsillar abscess. In the clinic, she was advised to "discontinue the useless and dangerous oral strophanthin preparation." She complied and, after her release, there was a prompt increase in the previous heart complaints. One capsule of Strodival three times daily was prescribed along with a Lanata preparation. After 14 days the patient reported feeling much better. After one month, she had only occasional cramps in the chest and was otherwise completely free of complaints.

III RURAL PRACTICE, NORTH WUERTTEMBURG, GERMANY

Case: A. G., male, 40 years old

The medical history showed frequent anginas, otitis, furunculosis, and scarlet fever with a very poor tendency to recover. An ECG taken shortly thereafter showed a marked ST depression in 2 and 1. There were some heart complaints, and an examination also showed traces of albumin in the urine and a slightly increased blood pressure of 145/100. High doses of an oral strophanthin were instituted a few years later because of massive heart complaints — stenocardia, insomnia, asthma with all exertion, and blood pressure of 235/135 and not below 230/130 after rest.

There was reasonably good tolerance to the medication. Blood pressure after one week was 190/130. In spite of an intervening infection, the previous complaints markedly decreased in the course of the following months; and there was no longer any pressure on the chest. Blood pressure later dropped to 170/90.

A change of Strodival was made. The blood pressure was maintained at 150/100 with one capsule 2 to 3 times daily (mostly swallowed). The patient was free of complaints and of the opinion that: "he feels more active than previously as a result of the red capsules."

IV MEDICAL OFFICER IN A COMMUNICATIONS BATALLION OF THE GERMAN ARMY

Case 1: first sergeant major, 36 years old

There was a medical history of hypertonicity for ten years, blood pressure around 170/90, and an infection of about 1 week duration with very poor recovery. The patient complained that: "Everything is such an effort". An examination showed severe stenocardia and accentuated P2.

The patient was successfully treated with a commercially available oral strophanthin preparation, but for only a few days. The medication was changed to Strodival (two capsules three times daily). The complaints subsided very quickly. There was no longer any pressure on the chest, respiration was freer, and sleep improved considerably. Blood pressure dropped to 160/90.

Since then the patient has taken Strodival as needed to keep his condition stable. He is completely capable of service. Blood pressure is 150/85.

Case 2: St., captain, 33 years old

Medical history — highly feverish, complicated measles at 29 years of age with a very long recovery. Since then the patient has had circulation complaints, uneasiness of the heart, vertigo, excessive heart beat, and heart burn. The patient later developed influenza, then increased stenocardia. His blood pressure was 160/90, and he had insomnia.

The patient was immediately given two capsules of Strodival three times daily. There was sudden decrease in all of the previous complaints. The patient is capable of service with Strodival, which is taken only when required.

V INTERNIST PRACTICE IN A LARGE CITY IN ISRAEL

Case 1: Mrs. B. H., housewife

For years the patient had high blood pressure (170/100) with anginal complaints, especially when mounting stairs; radiation in the back and arm; and attacks of angina pectoris. Past medication was Pentitraten and Reserpine and nitroglycerin in the case of an attack. An ECG clearly showed left heart damage, low T, and slightly low R-ST but otherwise nothing unusual.

Strodival (one capsule three times daily) was prescribed. After a few days, the patient's blood pressure was 150/85 without additional treatment. She reported that she was sleeping better than for a long time, had no further stenocardia, and felt fully productive.

The patient contracted a spasmodic infection after which she felt very poorly. The dosage of Strodival was increased to two capsules three times daily. This resulted in rapid recovery. Since then, the medication has been taken regularly or as required. A slight eructation "is gladly accepted". The latest ECG shows marked improvement and a higher T peak.

Case 2: M. D., female, teacher, 32 years old

A few weeks after a virus infection, the patient complained of tiredness, palpitations of the heart, pressure in the chest with even slight exertion, a craving for air, night sweat, restless sleep and very oppressive dreams. Blood pressure was 120/70 and pulse 84, and chamber extrasystoles appeared in the ECG. The patient was treated with Crataegus and high doses of Vitamin B. There was no improvement.

Two capsules of Strodival three times daily was then prescribed. This resulted in remarkably rapid improvement — disappearance of the chest pressure when walking, normal night rest, and infrequent extrasystoles. The medication was reduced to one capsule of Strodival three times daily. After another 5 weeks, the treatment was terminated.

At that time the ECG was completely normal, and there was no extrasystoles. Blood pressure was 115/75 and pulse about 75.

This was an example of typical left heart damage after viral pneumonia. The damage healed rapidly and completely under Strodival treatment.

Case 3: N. T., 72 years old, book expert, still working

High blood pressure was found about seven years previously, and an ECG was taken without diagnosis. The patient's blood pressure fluctuated between 200/100 and 160/90.

Three years prior to the beginning of Strodival therapy, the patient had an "attack." An ECG later showed an old anterior wall infarct. Digoxin was administered for 6 months. The patient did not feel well taking this medication. An examination showed a blood pressure of 190/100, cardial insomnia, a closed-in feeling, considerable tiring during the day, and from an ECG: chamber extrasystoles, low T-peak, and sinus arrhythmy.

Treatment with two capsules of Strodival three times daily was started immediately. After 2 weeks, blood pressure was 150/180.

Continuous further control with Strodival was exercised. After about 5 months, post examination blood pressure was 140/80. The ECG was improved, and there were only infrequent extrasystoles. All indications of the left insufficiency had diminished, and the patient was able to sleep through the night again. This condition was maintained with a maintenance dose taken as needed.

Case 4: P. N., 65 years old, merchant

For many years the patient had high blood pressure with all the classical indications of left insufficiency. Digoxin was previously administered without conclusive results. A subsequent examination showed a blood pressure of 210/115 and distinct left damage (from an ECG).

The patient was immediately given two capsules of Strodival three times daily, and all other treatment was terminated. His blood pressure, which had been considered cardiogenic from the beginning, normalized itself within a very short time to around 160/90. Also, the patient's complaints largely disappeared, and the will to work increased.

Medication with Strodival has been continued. The maintenance dose is about one capsule three times daily. In exceptional circumstances this is increased as high as nine capsules per day.

Case 5: Sch. J., 57 years old, office employee

For many years the patient had migrane and high blood pressure (generally around 200/100). In spite of continuous treatment, no reduction in the pressure was successfully accomplished. The patient also suffered considerable asthma with exertion, had pressure over the chest, found it impossible to lie flat or on the left side, and very quickly became fatigued. Treatment with digoxin was unsuccessful.

Left hypertrophy in the ECG, 2 PT clearly accentuated was found. Two capsules of Strodival three times daily was administered. After three weeks all complaints were markedly reduced, and the patient was especially impressed by a considerable alleviation of the past "migrane attacks". His blood pressure was 160/100.

After continuation of the treatment for approximately four months, an ECG showed no indications of stresses; and the patient's blood pressure had dropped to 150/90. The patient had not take any antihypertonica for months, his night rest was undisturbed, and there was a considerable improvement in the capability to work.

Case 6: S. S., 56 years old, owner of metal working plant

For many years, damage of the heart muscle had existed with very high blood pressure (up to 230/130). There was twitching of the eyes, closed-in feelings, and frequent angina pectoris attacks. The secondary diagnosis was spondylarthrocace and considerable auditory damage. The slightest physical exertions immediately caused asthma, and the patient had to practically sit in bed at night. Digitalis had been administered for many years.

The medication was changed from digitalis to Adelphan, Estaban, and similar preparations. At a subsequent examination the blood pressure was 190/115, and there was significant 2 PT in the ECG and very considerable left broadening. Only with much effort could the patient's condition be kept under control for extended periods.

About two years after the change in the medication the blood pressure was again 220/115, and night rest was very disturbed. The patient was ordered to take two capsules of Strodival two to three times daily and, initially, to continue the past treatment. In a very short time the blood pressure dropped to 165/90. The very severe symptoms were reduced. The patient needed little nitroglycerin at night, and angina pectoris attacks became infrequent. The patient could work again (for about four hours daily) without any significant ill effects.

Case 7: M. P., 61 years old, metal worker and manual laborer

The patient had high blood pressure for years. After severe physical and mental stress, there were "heart attacks with perspiration and oppressive respiration". The patient was referred to a clinic where a lateral infarct was found. He could again perform light work after four months rest and treatment.

At the time he came for treatment the initial diagnosis showed severe inner anxiety, depressed disposition, difficulty in sleeping, continuous anginous pressure over the heart, and inability to lie flat. The blood pressure was 180/120 and the pulse around 80. P 2 was strongly stressed, and there were isolated extrasystoles.

The patient was immediately switched to Valium and 6 capsules of Strodival per day. After 3 months of treatment, the blood pressure had decreased to 145/85. The patient was practically free of complaints but still cautioned against working. His ECG was almost normal.

After another 5 months of taking Strodival, the patient resumed work on his own initiative (4 to 5 hours per day). He felt "very good". Only with exertion did he have any pressure over the chest, this being accompanied by a slight radiation. The patient varied the Strodival dosage by himself as needed.

After 3 months the following was found: blood pressure 150/90, undisturbed night rest, and further mitigation of the former complaints. The patient was working over 6 hours daily and taking 5 to 8 capsules of Strodival daily as needed.

Because of diarrhea, the medication had to be discontinued twice. The first episode of diarrhea was treated with Mexaform. Strodival was tolerated well with the Mexaform.

The second occasion of diarrhea appears to have been the consequence of an enteritis.

The patient remains capable of working with a "sliding" Strodival treatment.

VI INTERNIST PRACTICE IN SOUTHERN GERMAN CITY

Case 1: physician, 49 years old

Very severe post-myocardic, permanent myocardium damage remained after almost fatal sepsis, causing frequent anginas and infections. There was a considerable lowering of productivity, frequent heart complaints, cardial disturbances of sleep, and coronary dilations. Digitalis and other conventional treatments were tried without success. The patient gave up his profession and entered public service for health reasons.

A change was made to an oral strophanthin preparation which considerably reduced all complaints. However, because of irritation to the mouth and stomach, the necessary dosage could frequently not be tolerated.

Later, a change to Strodival was made. There were no more symptoms of irritation even with high doses. The patient was completely productive in strenuous official service. As soon as the medication was discontinued, the complaints returned so further Strodival compensation therapy was continued.

Case 2: female physician, 59 years old

The patient had permanent myocardial damage after having had scarlet fever twice. Increasing left heart symptoms occurred over a period of ten years along with stenocardia spreading into the shoulder and back, rapid fatigue, asthma with exertion, and sleeping problems during the second half of the night. Cardiogenic hypertonicity of 200/100 was present, and the left side of the heart was considerably dilated. An ECG showed severe left ventricular damage of the inner layer.

Coronary dilatants were unsuccessful as was digitoxin. With digitoxin, there was an increase of the complaints up to "complete misery".

Finally, an oral strophanthin preparation was prescribed. Even on the first day there was a lessening of the heart complaints which had existed for years; the "complete misery" was replaced by a "pleasant freshness". However, the patient did not tolerate the preparation too well, was troubled with diarrhea, and had to discontinue the strophanthin medication.

The medication was changed to Strodival which the patient easily tolerates and takes as required. The patient swallows one capsule three times daily which maintains the same good condition. There are no sleeping problems, and she is completely productive. However, as soon as the medication is discontinued, the heart complaints recur.

Case 3: secretary, 39 years old

The patient has a cardiac enlargement of an unexplained type resulting from anamnestic scarlet fever. A severe left dilatation has been present for ten years. In the ECG, there is left branch block. There had been heart complaints for years, general slackness, rapid fatigue, asthma, and no motivation. The patient had "one or two lows" almost daily.

Following the administration of Strodival, the patient became physically and mentally active and vivacious and had no more heart complaints. Three to four capsules per day are sufficient to maintain this condition most of the time. In the case of special exertions, the dosage is increased somewhat. Inadvertent interruption of the medication results in the old complaints immediately appearing. When required, the capsules are masticated and sucked, which leads to a particularly rapid and convincing improvement.

Case 4: inmate of an old people's home, female, 80 years old

An examination showed an aged heart, left damage in the ECG, hypertonicity of 200/90, and damage due to overstresses of a previously damaged ventricle. The patient felt heart pressure even with very light exertion.

With strophanthin drops, there was a reduction in the blood pressure to 150/75 and clear improvement in physical and mental productivity. However, the medication frequently produced diarrhea, and rectal strophanthin treatment was not possible. As an expedient, Lanatosid C was used; but this did not have nearly as favorable an effect.

The medication was changed to Strodival. Two to three capsules daily were tolerated without any intestinal irritation. Optimum productivity was achieved. In spite of progressive aging, the patient became essentially free of physical and mental complaints and resumed long walks in the city.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed and desired to be secured by Letters Patent is:

1. An orally administrable medication for treating angina pectoris, heart collapse, hypertonicity, and arrhythmia which comprises g-strophanthin distributed in an oleophilic vehicle in an amount and concentration effective to produce a threshhold myocardial concentration of the g-strophanthin via absorption through mucous membranes, the concentration of the g-strophanthin in the oleophilic vehicle ranging from three to twenty percent based on the total weight of the medication, and said oleophilic vehicle containing from 60 to 90 percent by weight of a stable, physiologically harmless fatty oil or mixture of fatty oils; from 2 to 20 percent by weight of a wax or wax mixture for adjusting and stabilizing the physical properties of the vehicle; and a lecithin in an amount ranging from 2–20 percent by weight and sufficient to reduce the irritating effect of the strophanthin on mucous tissue and to stabilize the dispersion of the strophanthin in the vehicle.

2. An orally administrable medication for treating angina pectoris, heart collapse, hypertonicity, and arrhythmia comprising an ingestible capsule which contains g-strophanthin distributed in an oleophilic vehicle in an amount and concentration effective to produce a threshhold myocardial concentration of the g-strophanthin via absorption through mucous membranes, the concentration of the g-strophanthin in the oleophilic vehicle ranging from three to twenty percent based on the total weight of the medication, and said oleophilic vehicle containing from 60 to 90 percent by weight of a stable, physiologically harmlss fatty oil or mixture of fatty oils; from 2 to 20 percent by weight of a wax or wax mixture for adjusting and stabilizing the physical properties of the vehicle; and a lecthin in an amount ranging from 2–20 percent by weight and sufficient to reduce the irritating effect of the strophanthin on mucous tissue and to stabilize the dispersion of the strophanthin in the vehicle.

3. A method of treating a mammalian patient afflicted with a cardiac complaint selected from the group consisting of angina pectoris, heart collapse, hypertonicity, and arrhythmia which comprises the steps of administering orally and at least daily one or more capsules containing g-strophanthin distributed in an oleophilic vehicle in an amount and concentration effective to produce a threshhold concentration of the g-strophanthin capable of exerting a triggering action in the patient's myocardium via absorption through his mucous membranes, the concentration of the g-strophanthin in the oleophilic vehicle ranging from three to twenty percent based on the total weight of the medication, and said oleophilic vehicle containing from 60 to 90 percent by weight of a stable, physiologically harmless fatty oil or mixture of fatty oils; from 2 to 20 percent by weight of a wax or wax mixture for adjusting and stabilizing the physical properties of the vehicle; and a lecithin in an amount ranging from 2–20 percent by weight and sufficient to reduce the irritating effect of the strophanthin on mucous tissue and to stabilize the dispersion of the strophanthin in the vehicle.

4. The medication of claim 1, wherein the lecithin is present in an amount of not more than 10 percent by weight.

5. The medication of claim 1, wherein the vehicle contains, by weight:
beeswax — 3.7 percent
partially hydrogenated vegetable oils — 39.8 percent
hydrogenated soybean oil — 3.7 percent
soy lecithin — 5.0 percent
rape oil — 44.0 percent 6. The medication of claim 5, wherein the partially hydrogenated vegetable oils are glycerides of the following acids:
saturated fatty acids — 18–21 percent by weight
oleic acid — 72–76 percent by weight
linoleic acid — 1.3–3.0 percent by weight linolenic acid — 0.04–3.0 percent by weight
and have the following characteristics in toto:
acid number — <0.5
saponification number — ca. 185–195
iodine number — ca. 65–75
peroxy number — <1.0
melting point — ca. 43°–46° C.

7. The medication of claim 2, wherein the vehicle contains, by weight:
beeswax — 3.7 percent
partially hydrogenated vegetable oils — 39.8 percent
hydrogenated soybean oil — 3.7 percent
soy lecithin — 5.0 percent
rape oil — 44.0 percent.

8. The medication of claim 7, wherein the partially hydrogenated vegetable oils are glycerides of the following acids:
saturated fatty acids — 18–21 percent by weight
oleic acid — 72–76 percent by weight
linoleic acid — 1.3–3.0 percent by weight
linolenic acid — 0.04–3.0 percent by weight
and have the following characteristics in toto:
acid number — <0.5
saponification number — ca. 185–195
iodine number — ca. 65–75
peroxy number — <1.0
melting point — ca. 43°–46° C.

9. The method of claim 3 wherein the vehicle present in the orally administered medication contains, by weight:
beeswax — 3.7 percent
partially hydrogenated vegetable oils — 39.8 percent
hydrogenated soybean oil — 3.7 percent
soy lecithin — 5.0 percent
rape oil — 44.0 percent.

10. The method of claim 9 wherein the partially hydrogenated vegetable oils in the vehicle are glycerides of the following acids:
saturated fatty acids — 18–21 percent by weight
oleic acid — 72–76 percent by weight
linoleic acid — 1.3–3.0 percent by weight
linolenic acid — 0.04–3.0 percent by weight
and have the following characteristics in toto:
acid number — <0.5
saponification number — ca. 185–195
iodine number — ca. 65–75
peroxy number — <1.0
melting point — ca. 43°–46° C.

* * * * *